United States Patent [19]
Bernareggi et al.

[11] Patent Number: 5,721,228
[45] Date of Patent: Feb. 24, 1998

[54] RECTAL FLUNISOLIDE COMPOSITIONS FOR TREATING INFLAMMATORY INTESTINAL DISORDERS

[75] Inventors: Virgilio Bernareggi, Cologno Monzese; Maurizio Fano, Bresso; Alessandro Gagnoni, Milan, all of Italy

[73] Assignee: Valeas S.p.A. Industria Chimica E Farmaceutica, Milan, Italy

[21] Appl. No.: 436,291

[22] PCT Filed: Nov. 18, 1993

[86] PCT No.: PCT/EP93/03228

§ 371 Date: May 17, 1995

§ 102(e) Date: May 17, 1995

[87] PCT Pub. No.: WO94/12187

PCT Pub. Date: Jun. 9, 1994

[30] Foreign Application Priority Data

Nov. 20, 1992 [IT] Italy ................. MI92A2657

[51] Int. Cl.$^6$ ................................. A61K 31/58
[52] U.S. Cl. ................................. 514/174
[58] Field of Search ................................. 514/174

[56] References Cited

U.S. PATENT DOCUMENTS

| | | | |
|---|---|---|---|
| 3,124,571 | 3/1964 | Ringold et al. | 514/174 |
| 4,427,670 | 1/1984 | Ofuchi et al. | 514/174 |
| 4,552,872 | 11/1985 | Cooper et al. | 514/175 |

FOREIGN PATENT DOCUMENTS 0 278 174  8/1988  European Pat. Off. .

OTHER PUBLICATIONS

Physicians Desk Reference, 46th ed. pp. 2244–2245, 1992.
Craig et al., "Modern Pharmacology", pp. 15–16, 1982.
Takai, et al., "The Predominance of Flunisolide In The Topical Use Of Anti–Inflammatory Steroids", J. Pharmacobiodyn, vol. 5, No. 3, 1982, pp. 200–207 (Abstract)*.

*Primary Examiner*—Raymond Henley, III
*Attorney, Agent, or Firm*—Kenyon & Kenyon

[57] ABSTRACT

Topical rectal therapeutic composition containing, as the active ingredient, flunisolide and/or one or more ester derivatives of same, in combination with suitable excipients and/or diluents, for the treatment of inflammatory intestinal disorders.

12 Claims, No Drawings

RECTAL FLUNISOLIDE COMPOSITIONS FOR TREATING INFLAMMATORY INTESTINAL DISORDERS

This is a 371 of PCT/EP93/03228 filed Nov. 18, 1993.

FIELD OF THE INVENTION

The present invention relates to topical rectal therapeutic compositions containing, the as active ingredient, flunisolide and/or ester derivatives of same in combination with suitable excipients and/or diluents, for the treatment of inflammatory intestinal disorders.

STATE OF THE ART

Among all inflammatory intestinal diseases, ulcerative colitis is certainly the best known. It essentially affects the large intestine, in particular and most severely the rectum, but sometimes, either marginally or entirely, the colon too.

Other types of inflammatory intestinal diseases may affect the rectum and result in a mild ulcerative colitis or in a slightly different, but pathologically similar syndrome, such as proctitis and sigmoiditis.

Another inflammatory intestinal disease is the so-called Crohn's disease, which affects the large intestine only marginally.

A known treatment of the above pathologies consists in the systemic and topical administration of corticosteroids, such as hydrocortisone, betamethasone, and prednisolone.

However, the systemic administration of the aforesaid drugs produces serious side effects, mainly related to the interference with the hypothalamus-hypophysis-adrenal gland axis.

Also the topical administration of said corticosteroids causes interference with the hypothalamus-hypophysis-adrenal gland axis, since said drugs are inevitably absorbed by the systemic route. The side effects more frequently arising from the topical treatment of ulcerative colitis with the aforesaid traditional corticosteroids are: transient or prolonged depression of adrenal gland functionality, weight increase, acne, and facies lunaris. It is to be noted that a characteristic of ulcerative colitis is an inflammed intestinal mucosa, which facilitates the systemic absorption of the drugs which are usually administered over an extended period of time. Therefore, the need of developing a corticosteroid exerting a high therapeutic activity in the treatment of inflammatory intestinal diseases and involving a reduced systemic absorption was deeply felt.

Takai et al. (J. Pharmacobiodyn. vol. 5, no. 3, 1982, pages 200–207, database Medline abstract) teach that flunisolide is highly active in topical use, while systemically it is relatively weak; these characteristics could be attributable to its rapid metabolic inactivation in the liver. Nevertheless it gives no indication of the absorption levels of fluticasone and its noxious effects, and there is no suggestion that it would be of use in treating inflammatory intestinal disorders.

Flunisolide is a corticosteroid having formula

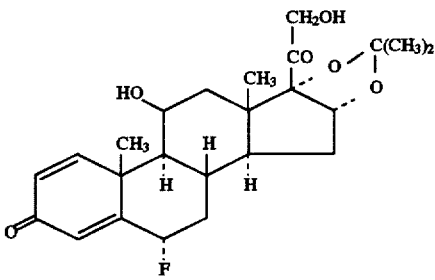

and is used for the treatment of asthma chiefly as nasal and bronchial topical preparations, of glaucoma as ophthalmic topical preparations, of allergic or inflammatory conditions of the skin as creams and ointments.

This molecule is characterized by not high absorption levels and by a metabolic process (hepatic first pass) which rapidly transforms same into the metabolite 6-β-hydroxyderivative, whose glucocorticoid activity is approx. 350 times lower than that of flunisolide.

In other words, the amount of flunisolide inevitably absorbed by the systemic way after topical application can never reach plasma levels interfering with the hypothalamus-hypophysis-adrenal gland axis.

THE PRESENT INVENTION

It has surprisingly been found that flunisolide and its esters administered by the topical rectal way are very active in the treatment of the aforesaid intestinal disorders and—unlike the steroids known so far—do not cause the adverse effects related to the interference with the hypothalamus-hypophysis-adrenal gland axis.

In fact, clinical trials carried out by the Applicant evidenced that an improvement of the basal symptomatology was obtained as early as after a 15-day topical rectal treatment at doses of 2 mg/die and that a 3-mg/die administration for 30 days did not cause any appreciable clinical modification to cortisol plasmatic concentrations, an indicator of the interference, if any, with the hypothalamus-hypophysis-adrenal gland axis.

Object of the present invention is, therefore, a topical rectal therapeutic composition containing, as active ingredient, flunisolide and/or one or more ester derivatives of same, in combination with suitable excipients and/or diluents, for the treatment of inflammatory intestinal disorders.

DETAILED DESCRIPTION OF THE INVENTION

The flunisolide used for the compositions of this invention is either anhydrous or in the corresponding hemihydrated form.

The expression "flunisolide ester derivatives" is used herein to mean the derivatives in which one or both hydroxylic functions in positions 11 and 21 of the aforesaid active ingredient have been esterified with $C_2$–$C_{20}$ alkyl-, aryl- or arylalkyl- mono and/or polycarboxylic acids, with alkyl- or aryl mono and/or polysulphonic acids, aryl acids containing one or more carboxylic functions and one or more sulphonic functions and, in case of carboxylic and/or sulphonic polyfunctional acids, the remaining acid functions are either partially or completely salified with pharmaceutically acceptable cations, preferably sodium, potassium, magnesium, calcium.

Particularly preferred flunisolide esters are those formed with acetic acid, propionic acid, hexanoic acid, meta-sulfobenzoic acid and relative sodium meta-sulfobenzoate.

The compositions of the present invention are preferably in the form of enemas, suppositories, and foams.

The suppositories of this invention contain from 0.5 to 10 mg each, preferably from 1 to 5 mg each of flunisolide and/or its ester derivatives.

In addition to the active ingredient, the suppositories of the present invention contain excipients preferably consisting of semisynthetic solid glycerides of vegetable saturated fatty acids.

The rectal enemas of this invention are generally liquid compositions, solutions, emulsions or aqueous suspensions having an active ingredient content from 0-5 to 10 mg each, more preferably from 1 to 5 mg each, and generally containing preservatives, preferably selected among Parabens, chelating agents, such as for example ethylenediaminetetraacetic acid or the relative sodium salt. Should said enemas be emulsions or suspensions, they would also contain thickeners, such as carboxymethylcellulose, and should they be solutions they would contain thickeners-solubilizers, such as propylene glycol.

Said enemas may also contain compounds acting as pH regulators, preferably mineral or organic acids and/or pharmaceutically acceptable salts.

The rectal foams have an active ingredient content preferably from 0.5 to 10 mg/dose more preferably from 1 to 5 mg unitary dose.

Preferably, the rectal foams of this invention also contain:

- traditional solubilizers, such as purified water and propylene glycol (the latter also acts as a thickener and is used for enemas) and solubilizers also protecting the skin, essentially consisting of partial glycerides of polyoxyethylenic saturated fatty acids;
- emulsifiers, such as polysorbate 20 and mixtures of cetostearylic alcohol with sorbitan esterified with polyoxyethylenic fatty acids;
- chelating agents, such as ethylenediaminetetraacetic acid, also in the form of sodium salt;
- preservatives, such as Parabens—also used for enemas;
- acidifying buffers, such as phosphoric acid and monobasic sodium or potassium phosphate;
- propellants, such as hydrocarbons, e.g. isobutane, or fluorocarbons, e.g. dichlorodifluoromethane and dichlorotetrafluoroethane, or hydrochlorofluorocarbons or hydrofluorocarbons.

As concerns the pharmaceutical formulation, rectal foams—compared with enemas—have a lower water content and contain propellants, which are indispensable for dispensing the dose of drug to be administered.

It is just the presence of propellants that allows the dose dispensed at each release of the pressure valve—in case of multidose bottles—or on pressure release valve—in case of single-dose bottles—to spread out and reach the inmost regions of the intestine, e.g. the colon left splenic flexure.

The propelling properties can vary depending on the type and quantity of propellant used and, consequently, the foam can reach more or less distant regions of the intestine.

The following examples of therapeutic compositions for topical rectal use that are the object of this invention are conveyed by way of indication, not of limitation.

A) Rectal foam

1) One 14-dose pressure bottle (2 mg anhydrous flunisolide/dose) and one single-dose (2 mg anhydrous flunisolide) pressure bottle contain:

|  | Multidose | Single-dose |
|---|---|---|
| Anhydrous flunisolide | 28 mg | 2 mg |
| Cetostearylic alcohol + sorbitan polyoxyethylenic esters | 830 mg | 59.3 mg |
| Polysorbate 20 | 553 mg | 39.5 mg |
| Propylene glycol | 11.38 g | 956 mg |
| Glycerides of polyoxyethylenic saturated fatty acids | 6.85 | 489 mg |
| Purified water | 10.17 g | 726 mg |
| Methyl p-hydroxybenzoate | 39.5 mg | 2.8 mg |
| Propyl p-hydroxybenzoate | 7.9 mg | 0.56 mg |
| Ethylenediaminetetraacetic acid disodium salt | 15.8 mg | 1.13 mg |
| Monobasic sodium phosphate Phosphoric acid q.s. to pH 5 | 313 mg | 22.4 mg |
| Dichlorodifluoromethane | 2.53 g | 616 mg |
| Dichlorotetrafluoroethane | 3.79 g | 922 mg |

2) One 14-dose pressure bottle (2 mg hemihydrated flunisolide/dose) and one single-dose (2 mg hemihydrated flunisolide) pressure bottle contain:

|  | Multidose | Single-dose |
|---|---|---|
| Hemihydrated flunisolide | 28.58 mg | 2.04 mg |
| Cetostearylic alcohol + sorbitan polyoxyethylenic esters | 830 mg | 59.3 mg |
| Polysorbate 20 | 553 mg | 39.5 mg |
| Propylene glycol | 13.38 g | 956 mg |
| Glycerides of polyoxyethylenic saturated fatty acids | 6.85 g | 489 mg |
| Purified water | 10.17 g | 726 mg |
| Methyl p-hydroxybenzoate | 39.5 mg | 2.8 mg |
| Propyl p-hydroxybenzoate | 7.9 mg | 0.56 mg |
| Ethylenediaminetetraacetic acid disodium salt | 15.8 mg | 1.13 mg |
| Monobasic sodium phosphate Phosphoric acid q.s. to pH 5 | 313 mg | 22.4 mg |
| Dichlorodifluoromethane | 2.53 g | 616 mg |
| Dichlorotetrafluoroethane | 3.79 g | 922 mg |

3) One 14-dose pressure bottle (2 mg anhydrous flunisolide/dose) and one single-dose (2 mg anhydrous flunisolide) pressure bottle contain:

|  | Multidose | Single-dose |
|---|---|---|
| Anhydrous flunisolide | 28 mg | 2 mg |
| Cetostearylic alcohol + sorbitan polyoxyethylenic esters | 830 mg | 59.3 mg |
| Polysorbate 20 | 553 mg | 39.5 mg |
| Propylene glycol | 13.38 g | 956 mg |
| Glycerides of polyoxyethylenic saturated fatty acids | 6.85 g | 489 mg |
| Purified water | 10.17 g | 726 mg |
| Methyl p-hydroxybenzoate | 39.5 mg | 2.8 mg |
| Propyl p-hydroxybenzoate | 7.9 mg | 0.56 mg |
| Ethylenediaminetetraacetic acid disodium salt | 15.8 mg | 1.13 mg |
| Monobasic sodium phosphate Phosphoric acid q.s. to pH 5 | 313 mg | 22.4 mg |
| Isobutane | 3.16 g | 769 mg |

4) One 14-dose pressure bottle (2 mg hemihydrated flunisolide/dose) and one single-dose (2 mg hemihydrated flunisolide) pressure bottle contain:

|                               | Multidose | Single-dose |
| --- | --- | --- |
| Hemihydrated flunisolide | 28.58 mg | 2.04 mg |
| Cetostearylic alcohol + sorbitan polyoxyethylenic esters | 830 mg | 59.3 mg |
| Polysorbate 20 | 553 mg | 39.5 mg |
| Propylene glycol | 13.38 g | 956 mg |
| Glycerides of polyoxyethylenic saturated fatty acids | 6.85 g | 489 mg |
| Purified water | 10.17 g | 726 mg |
| Methyl p-hydroxybenzoate | 39.5 mg | 2.8 mg |
| Propyl p-hydroxybenzoate | 7.9 mg | 0.56 mg |
| Ethylenediaminetetraacetic acid disodium salt | 15.8 mg | 1.13 mg |
| Monobasic sodium phosphate | 313 mg | 22.4 mg |
| Phosphoric acid q.s. to pH 5 | | |
| Isobutane | 3.16 g | 769 mg |

B) Suppositories

5) One suppository (2 mg anhydrous flunisolide) contains:

| Anhydrous flunisolide | 2 mg |
| --- | --- |
| Glyceric esters of saturated fatty acids | 1498 mg |

6) One suppository (2 mg hemihydrated flunisolide) contains:

| Hemihydrated flunisolide | 2.04 mg |
| --- | --- |
| Glyceric esters of saturated fatty acids | 1498 mg |

C) Enema

7) One 60 ml single-dose bottle (2 mg anhydrous flunisolide) contains:

| Anhydrous flunisolide | 2 mg |
| --- | --- |
| propylene glycol | 24 g |
| Ethylenediaminetetraacetic acid sodium salt | 15 mg |
| Hydrochloric acid | q.s. to pH 5 |
| Purified water | q.s. to 60 ml |

8) One 60 ml single-dose bottle (2 mg hemihydrated flunisolide) contains:

| Hemihydrated flunisolide | 2.04 mg |
| --- | --- |
| Propylene glycol | 24 g |
| Ethylenediaminetetraacetic acid sodium salt | 15 mg |
| Hydrochloric acid | q.s. to pH 5 |
| Purified water | q.s. to 60 ml |

The excipients of the above compositions are reported below.

Rectal foam

| EXCIPIENT | FUNCTION |
| --- | --- |
| Cetostearyl alcohol containing sorbitan esterified with polyoxyethylenic fatty acids | emulsifier |
| Polysorbate 20 | emulsifier |
| Partial glycerides of polyoxyethylenic saturated fatty acids | solubilizer-skin protector |
| Propylene glycol | solubilizer-thickener |
| Methyl p-hydroxybenzoate sodium salt | preservative |
| Propyl p-hydroxybenzoate sodium salt | preservative |
| Ethylenediaminetetraacetic acid disodium salt | chelating agent |
| Purified water | solubilizing vehicle |
| Monobasic sodium phosphate and phosphoric acid | pH regulating buffer |
| Dichlorodifluoromethane | propellant |
| Dichlorotetrafluoroethane | propellant |
| Isobutane | propellant |

Suppository

| EXCIPIENT | FUNCTION |
| --- | --- |
| Semisynthetic solid glycerides | mass for suppository (solid vehicle) |

Enema

| EXCIPIENT | FUNCTION |
| --- | --- |
| Propylene glycol | solubilizer-thickener |
| Ethylenediaminetetraacetic acid sodium salt | chelating agent |
| Hydrochloric acid | acidifier |
| Purified water | solubilizing vehicle |

CLINICAL TRIALS

FLUNISOLIDE ENEMA (2 and 3 mg)

Preliminary clinical trials were conducted with Flunisolide in the form of enema using No. 18 patients of both sexes suffering from ulcerative colitis, limited to the splenic flexure. Patients were divided into two groups and treated with 2 mg/die and 3 mg/die, respectively, for 30 days.

The obtained results clearly indicate that the drug has an excellent therapeutic efficacy and above all is well tolerated, especially in relation to the inferference with the hypothalamus-hypophysis-adrenal gland axis.

In particular treatments with Flunisolide at a dose of 2 mg/die and 3 mg/die for 15 and 30 days always produced statistically significant improvements (Mann-Whitney's "U" test) of the basal sympotomatology as far as the clinical and the sigmoidoscopic parameters are concerned (cf. Table 1 attached hereto).

As concerns drug toleration to the treatment and in particular the interference with the hypothalamus-hypophysis-adrenal gland axis, the treatment with flunisolide at the higher dose (3 mg/die) for 30 days never determined cortisolemia values below normality.

TABLE 1

Average values ± standard error of the mean of scores detected basally ($T_0$) and after 15 ($T_{15}$) and 30 ($T_{30}$) days of treatment with flunisolide at the dose of 2 and 3 mg/die. Results of the statistical evaluation made by Mann-Whitney's "U" test compared with the respective basal values.
(score 1 = normal; score 2 = mild; score 3 = moderate)

| PARAMETERS | $T_0$ | $T_{15}$ | $T_{30}$ |
|---|---|---|---|
| Flunisolide 2 mg/die (No. 10) | | | |
| CLINICAL | 2.7 ± 0.2 | 1.9 ± 0.2 * | 1.5 ± 0.2 ** |
| SIGMOIDOSCOPIC | 2.7 ± 0.2 | 2.2 ± 0.1 * | 1.6 ± 0.2 ** |
| Flunisolide 3 mg/die (No. 8) | | | |
| CLINICAL | 2.9 ± 0.1 | 2.0 ± 0.2 ** | 1.6 ± 0.2 ** |
| SIGMOIDOSCOPIC | 3.0 ± — | 2.4 ± 0.2 ** | 2.1 ± 0.2 ** |

*P ≦ 0.05;
**P ≦ 0.01

We claim:

1. A method of locally treating inflammatory intestinal diseases comprising administering to a patient in need of such treatment a pharmaceutically effective amount of flunisolide or a flunisolide ester, said pharmaceutically effective amount being administered by a topical rectal route.

2. Therapeutic method for the treatment of ulcerative colitis, inflammatory intestinal diseases resulting in mild ulcerative colitis or in a slightly different, but pathologically similar syndrome or of Chron's disease, comprising the topical, rectal application of a pharmaceutical composition containing as active ingredient anhydrous or hemihydrated flunisolide and/or one or more ester derivatives of same, in combination with suitable excipients and/or diluents, said pharmaceutical composition containing between 0.5 and 1 mg of active ingredient per unitary posological dose.

3. Therapeutic method according to claim 2 wherein the unitary posological dose is between 1 and 5 mg.

4. Therapeutic method according to claim 2 wherein the pharmaceutical composition is in the suppository form.

5. The therapeutic method according to claim 4 wherein said suppository form contains excipients selected from the group consisting of semisynthetic glycerides of vegetable saturated fatty acids.

6. The therapeutical method according to claim 2 wherein the pharmaceutical composition is in the rectal enema form.

7. The therapeutic method according to claim 6 wherein said rectal enema form is a solution, which contains preservatives chelating agents, pH regulators and thickeners-solubilizers.

8. The therapeutic method according to claim 6 wherein said rectal enema form is an emulsion or an aqueous suspension, which contains preservatives chelating agents, and thickeners-emulsifiers.

9. The therapeutic method according to claim 2 wherein the pharmaceutical composition is in the rectal foam form.

10. The therapeutic method according to claim 9 wherein said rectal foam form further comprises emulsifiers, water, thickeners-solubilizers, and thickeners-solubilizers also exerting a skin protective action, preservatives, chelating agents, acidifying buffers, and propellents.

11. The therapeutic method according to claim 2 wherein the flunisolide ester derivatives are those having one or both hydroxylic functions in positions 11 and 21 of the aforesaid active ingredient eserified with $C_2$–$C_{20}$ alkyl-, aryl- or arylalkyl- mono and/or polycarboxylic acids, with alkyl- or aryl mono and/or polysulphonic acids, aryl acids containing one or more carboxylic functions andone or more sulphonic functions and, in case of carboxylic and/or sulphonic polyfunctional acids, the remaining acid functions are either partially or completely salified with pharmaceutically acceptable cations.

12. The therapeutic method according to claim 2 wherein the used flunisolide esters are the esters formed with acetic acid, propionic acid, hexanoic acid, meta-sulfobenzoic acid and relevant sodium meta-sulfobenzoate.

* * * * *